United States Patent
Fang et al.

(10) Patent No.: US 10,253,285 B2
(45) Date of Patent: Apr. 9, 2019

(54) METHOD FOR SIMULTANEOUSLY REDUCING URETHANE AND ITS PRECURSORS LEVELS DURING CHINESE LIQUOR PRODUCTION PROCESS

(71) Applicant: Jiangnan University, Wuxi (CN)

(72) Inventors: Fang Fang, Wuxi (CN); Xia Ding, Wuxi (CN); Qiaoyu Li, Wuxi (CN); Fan Liu, Wuxi (CN); Xinhu Zhou, Wuxi (CN); Xiang Chen, Wuxi (CN); Jian Chen, Wuxi (CN); Guocheng Du, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 15/794,048

(22) Filed: Oct. 26, 2017

(65) Prior Publication Data

US 2018/0112163 A1    Apr. 26, 2018

(30) Foreign Application Priority Data

Oct. 26, 2016 (CN) ........................... 2016 1 0944887
Oct. 26, 2016 (CN) ........................... 2016 1 0948286

(51) Int. Cl.
    *C12G 3/08*      (2006.01)
    *C12N 1/20*      (2006.01)
    *C12N 9/54*      (2006.01)
    *C12R 1/07*      (2006.01)

(52) U.S. Cl.
    CPC ................ *C12G 3/08* (2013.01); *C12N 1/20* (2013.01); *C12N 9/54* (2013.01); *C12R 1/07* (2013.01); *C12Y 305/01005* (2013.01)

(58) Field of Classification Search
None
See application file for complete search history.

(56) References Cited

FOREIGN PATENT DOCUMENTS

KR      2015019435 A    *    2/2015

OTHER PUBLICATIONS

Zhang et al. Characterization of a Bacillus amyloliquefaciens strain for reduction of citrulline accumulation during soy sauce fermentation., BioTechnol Lett, 2016 (EPub Jun. 20, 2016), 38: 1723-1731.*
Coukoulis et al. Transformation in Bacillus amyloliquefaciens, Journal of Bacteriology (1971), 102: 319-322.*
Rensburg et al. Enzymes in winemaking: harnessing natural catalysts for efficient biotransformation—a review, S. Afr. J. Enol. Vitic., vol. 21, special Issue, 2000, p. 52-73).*
Idriss et al. Extracellular phytase activity of Bacillus amyloliquefaciens FZB45 contributes to its plant-growth-promoting effect, Microbiology (2002), 148: 2097-2109.*

* cited by examiner

*Primary Examiner* — Iqbal H Chowdhury
(74) *Attorney, Agent, or Firm* — Na Xu; IPro, PLLC

(57) ABSTRACT

The present invention a method for simultaneously reducing urethane and its precursors levels during Chinese liquor production process, which relates to the field of fermented food production. The present invention is carried out through inoculating *Bacillus amyloliquefaciens* JP21 or combines with urease into the grains for fermentation. The content of EC and urea in the fermented grains after 5-day fermentation could reduce 30.16% and 50.05% respectively, With an addition of the *B. amyloliquefaciens* during grains fermentation, EC and urea levels are successfully controlled, and at the same time aroma and tastes of Chinese liquor hasn't been affected.

8 Claims, 2 Drawing Sheets

METHOD FOR SIMULTANEOUSLY REDUCING URETHANE AND ITS PRECURSORS LEVELS DURING CHINESE LIQUOR PRODUCTION PROCESS

CROSS-REFERENCES AND RELATED APPLICATIONS

This application claims the benefit of priority to Chinese Application No. 201610944887.9, entitled "A method for simultaneously reducing urethane and its precursors levels in fermented grains of liquor", filed Oct. 26, 2016, and Chinese Application No. 201610948286.5, entitled "A Bacillus amyloliquefaciens that degrades urethane and urea", filed Oct. 26, 2016, which are herein incorporated by reference in its entirety.

BACKGROUND OF THE INVENTION

Field of the Invention

The present invention relates to a method for simultaneously reducing urethane and its precursors levels during Chinese liquor production process, which relates to the field of beverages fermented foods production.

Description of the Related Art

Ethyl carbamate (EC) is a toxic contaminant that has been widely detected in fermented foods and alcoholic beverages. The World Health Organization's International Agency for Research on Cancer (IARC) classified EC as a group 2A carcinogen, which suggests a potential carcinogenic risk to human.

It has been reported that alcoholic beverages (especially distilled spirits) were highly likely to contribute to EC intake for human. Chinese liquor, a branch of the distilled spirits, is the traditional spirits in China. During the long river of history, a large amount of consumers have been attracted by the well-known characteristic of Chinese liquor such as aromatic flavor and taste. Nevertheless, more data shows that, there is a considerable problem that EC is formed during the production process of Chinese liquor.

To date, two pathways have been reported for the formation of EC in Chinese liquor production. The reaction between urea and ethanol is the most common pathway of EC formation found in most of the fermented beverages. Urea reacts with ethanol under acidic condition, or converts to isocyanate or cyanate under thermolysis and then react with ethanol. The other one is cyanate, oxidized by cyanide, which reacts with ethanol. According to researches of EC formation mechanism, the majority of EC in the liquor is generated through the chemical reaction from urea and ethanol. Thus, methods for reducing EC can be realized through directly eliminating EC precursors and EC that has already been formed by microbial consumption. However, since the acid environment of Chinese liquor fermentation and the special production process, few functional strains have been found useful for EC elimination in Chinese liquor.

The most important point shall be clarified in this part is: EC is stable, it cannot be eliminated. Distillation stimulates the formation of EC from ethanol and its precursors (urea and citrulline). Thus, the most efficient way to reduce or eliminated EC is to decrease EC precursors in fermented grains prior to distillation.

DETAILED DESCRIPTION

The goal of the present invention is to provide a method for reducing EC and its precursors levels, comprising inoculating $1\sim9\times10^7$ CFU/g Bacillus amyloliquefaciens during the grain fermentation.

In one embodiment of the present invention, the wherein said B. amyloliquefaciens is inoculated before the grain fermentation begins.

In one embodiment of the present invention, 5~10 mL cell suspension/100 g grains of B. amyloliquefaciens is inoculated into the grains for fermentation.

In one embodiment of the present invention, the wherein said B. amyloliquefaciens is B. amyloliquefaciens JP21, which is deposited in China Center for Type Culture Collection in Wuhan University, Wuhan, Hubei, China on Sep. 19, 2016 with Accession CCTCC No: M 2016499.

In one embodiment of the present invention, the B. amyloliquefaciens is obtained from inoculating into the LB medium and incubating at 37° C. for 24~48 h.

In one embodiment of the present invention, the wherein said B. amyloliquefaciens combines with urease are added before the grain fermentation begins.

In one embodiment of the present invention, the urease is produced from Lactobacillus reuteri.

In one embodiment of the present invention, the method comprising the steps of: 1) B. amyloliquefaciens collection: the B. amyloliquefaciens is inoculated into LB medium, incubated at 37° C. for 24~48 h; the resulting broth is centrifuged, stain pellet is collected and then resuspended in 0.85% (w/v) NaCl; 2) strain inoculation: the B. amyloliquefaciens cells suspension is mixed with the grains at the concentration of $1\sim9\times10^7$ CFU/g; 3) grains fermentation: the whole fermentation process is under 28~30° C.

In one embodiment of the present invention, the method comprising the steps of: 1) strain inoculation: the B. amyloliquefaciens cells suspension is inoculated into the grains for fermentation at concentration of $1\sim9\times10^7$ CFU/g, the volume of the B. amyloliquefaciens suspension is 5~10 mL/100 g grains; 2) grains fermentation: the whole fermentation process is under 28~30° C.

The present invention provides a method for simultaneously reducing EC and its precursors in Chinese liquor production process through inoculating B. amyloliquefaciens JP21 or combines with urease into the grains for fermentation. The content of EC and urea in the fermented grains after 5-day fermentation could reduce 30.16% and 50.05% respectively. With an addition of the B. amyloliquefaciens during grains fermentation, EC and urea levels are successfully controlled, and at the same time aroma and tastes of Chinese liquor hasn't been affected.

BRIEF DESCRIPTION OF DRAWINGS

Figure Captions

DETAILED DESCRIPTION

Figure 1:
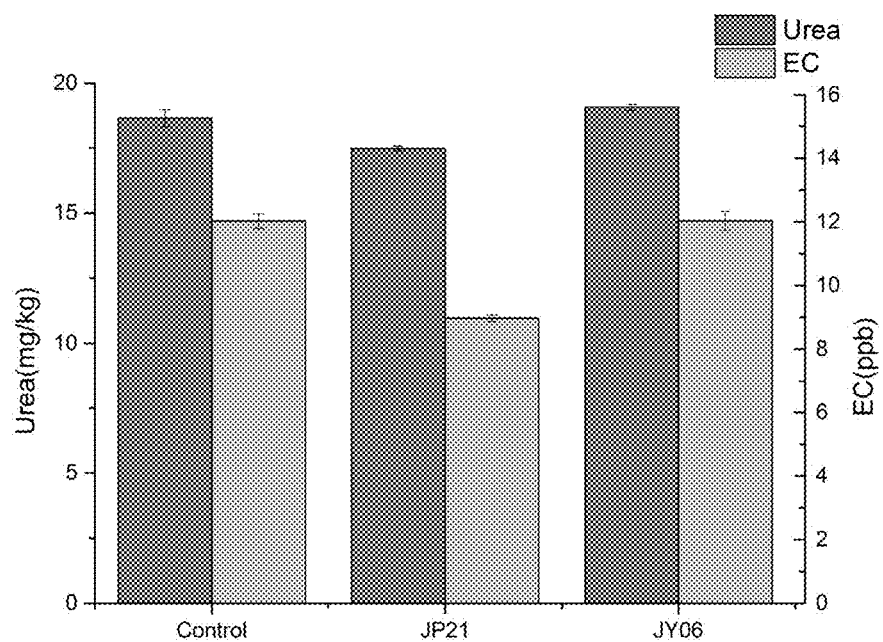
FIG. 1. EC and urea concentration of fermented grains that inoculated with B. amyloliquefaciens JP21 ($1\sim9\times10^6$ CFU/g) and B. amyloliquefaciens JY06 ($1\sim9\times10^6$ CFU/g) respectively.

Materials and Methods:

1. Urease Assay:

1) Construction of standard curve: 4 g/L ammonium chloride with volume of 0.2, 0.4, 0.6, 0.8, 1.0, 1.2, 1.4 or 1.6 mL is mixed with distilled water to a final volume of 2 mL; 1 mL 10% acetocaustin is added so the reaction is terminated. 1 mL chromogenic agent I and 1 mL chromogenic agent II are added before incubated at 37° C. for 20 min; ultrapure water is added to the resulting solution to a final volume of 10 mL, and then absorbance of the solution is measured at 578 nm.

2) Determination of samples: 1 mL enzyme and 1 mL 3% urea is mixed and incubated at 37° C. for 15 min, 1 mL 10% acetocaustin is added so the reaction is terminated; chromogenic agent I and 1 mL chromogenic agent II are added before incubated at 37° C. for 20 min; ultrapure water is added to the resulting solution to a final volume of 10 mL and absorbance of 578 nm is measured.

Chromogenic agent I: 15 g phenol and 15 g sodium nitroferricyanide are dissolved and diluted to a constant volume of 250 mL, stored at 4° C.

Chromogenic agent II: 13.125 g NaOH and 7.5 mL sodium hypochlorite are dissolved and diluted to a constant volume of 250 mL, stored at 4° C.

Enzyme activity is calculated through the formula below:

$$\text{Enzyme activity} = \frac{A \times n}{15 \times k} (U/mL);$$

A: UV spectrophotometric value; n: Dilution times; k: slope of standard curve.

2. Urethanase Assay:

1 mL of urethanase and 1 mL 3% urethane is mixed and incubated at 37° C. for 15 min, then 1 mL 10% acetocaustin is added to terminate the reaction; chromogenic agent I and 1 mL chromogenic agent II are added before incubated at 37° C. for 20 min; ultrapure water is added to the resulting solution to a final volume of 10 mL, and then the absorbance of the solution is measured at 578 nm. The enzyme activity is calculated according to the formula below:

$$\text{Enzyme activity} = \frac{A \times n}{15 \times k} (U/mL);$$

A: UV spectrophotometric value; n: Dilution times; k: slope of standard curve.

The standard curve is prepared with the same procedure with that of urea assay with the replacement of ethyl carbamate to urea.

3. Determination of Urea in Broth (EXAMPLE 3):

1 mL of microbial culture is centrifuged at 8000 rpm, 400 μL supernatant, 600 μL xanthydrol and 100 μL 0.1 moL/L HCl are mixed and react in dark for 30 min, then 0.22 m organic filter membrane is used for filtration before determination. The method of determination is disclosed in the paper that published on March 2011 with name of Determination of urea in rice wine by high performance liquid chromatography fluorescence detector.

4. Determination of EC in Broth (EXAMPLE 4):

4 mL of microbial culture is centrifuged at 8000 rpm, 2 mL supernatant and 100 μL D5-ethyl carbamate are mixed and then transferred to extraction column for 15 min standing. 15 mL dichloromethane solution is used to elute at about 1 mL/min flow rate, the eluted solution is concentrated by nitrogen to 0.5 mL at room temperature and subsequently add methanol to constant volume of 2.00 mL, after been purified by 0.45 μm organic membrane, the result solution is obtained for GC-MS the analysis. The method for determination of ethyl carbamate is according to Chinese national food safety standards with code of GB 5009.223-2014.

5. Determination of EC or Urea in Fermented Grains (EXAMPLE 5):

1) determination of urea: 10 g fermented grains and 20 mL sterile water are mixed and ice incubated for 30 min under sonic oscillator treatment, the resulting mixture is centrifuged at 8000 rpm for 5 min, supernatant is collected for HPLC analysis. The method of analysis is disclosed in the paper that published on March 2011 with name of determination of urea in rice wine by high performance liquid chromatography fluorescence detector.

2) determination of EC: 10 g fermented grains and 20 mL sterile water are mixed and incubated for 30 min, then sonic oscillator treated for 30 min, the resulting mixture is centrifuged at 8000 rpm for 5 min, supernatant is collected for EC analysis. The method for determination of ethyl carbamate is according to Chinese national food safety standards with code of GB 5009.223-2014.

Example 1: Isolation of *B. amyloliquefaciens* JP21

1. Strain Isolation and High Throughput Screening;

(1) Isolation of microbes in fermented grains: 0.85% saline and fermented grains is mixed at quality ratio of 1:1.6, the suspension is gradient diluted and plated on the MRS agar medium and YPD agar plate, respectively. The MRS medium is placed at 37° C., and the YPD medium is placed at 30° C. for at least 24 h until single colonies appeared on the plate.

(2) Isolation of strains with capability of utilizing urea or urethane: The colonies on MRS medium and YPD medium are transferred to MRS medium and YPD medium. Both MRS and YPD medium contains 10 g/L urea or urethane, respectively. The strains that been transferred to MRS medium are incubated at 37° C. and the strains been transferred to YPD medium are incubated at 30° C.

(3) Picking and cultivation of strains: 250 μL MRS medium is added into each well of 96-well plate, colony been surrounded with purple circle on the plate is transferred to 96-well plate using QPix420 automated microbial screening system, each colony is transferred to three wells and separately incubated at the optimal condition for 24 h. The culture broth is centrifuged at 6000 rpm for 10 min; strain cells are resuspensed with saline and transferred with 1% inoculation amount to medium containing chromogenic agent and urea or urethane. After been incubated for 24 h, strains in the color-changed well that changed from yellow to purple are the candidate strains.

2. Identification of the Strains:

the candidates are streaked and incubated to colonies, a single colony is transferred to MRS medium and incubated at 37° C. for 24 h; strains are collected, genome of the strain is extracted. The 16S rDNA sequence of the candidate strain is amplified using universal primers. From the blast results from NCBI database, the strain has high homology with *B. amyloliquefaciens*, and is designated as *B. amyloliquefaciens* JP21.

Example 2: Enzyme Production of *B. amyloliquefaciens* JP21

(1) Enzyme preparation: *B. amyloliquefaciens* JP21 (been screened from EXAMPLE 1) and *B. amyloliquefaciens* JY06 (been screened from the soy sauce mash, with code CCTCC No: M 2015423.) are both incubated in the medium at 37° C. for 24 h. 50 mL culture broth is centrifuged at 4000 rpm for 10 min, supernatant has been discard and cells precipitate are collected, the precipitate is washed by citrate buffer solution for twice, resuspended by 50 mL solution, and then ice incubated for 30 min before cell broken for 120 s, thus crude enzyme is obtained.

(2) Enzyme assay: The activity of urease and urethanase of the crude enzyme is determined. As it shows that the urease produced from *B. amyloliquefaciens* JP21 is 0.46 U/mL, and the urethanase is 0.28 U/mL, while no urease or urethanase activity has been detected from crude enzyme produced by *B. amyloliquefaciens* JY06.

Example 3: Degradation of Urea by *B. amyloliquefaciens* JP21

(1) Seed culture preparation: *B. amyloliquefaciens* JP21 and *B. amyloliquefaciens* JY06 are both incubated in the medium at 37° C. for 24 h. 50 mL culture broth is centrifuged at 4000 rpm for 10 min, supernatant has been discard and cells precipitate are collected, the precipitate is washed by citrate buffer solution for twice, resuspended by 50 mL solution, and then seed culture is obtained.

(2) Inoculation and grains fermentation: The seed culture (with the strain concentration of $6 \times 10^7$ CFU/mL) is inoculated at 1% volume ratio into the medium containing 10 g/L urea and 5 g/L glucose, and then incubated at 37° C. for 24 h. The urea concentration in the culture broth is detected through HPLC.

(3) Results: It is found that, urea in culture broth of *B. amyloliquefaciens* JP21 is 8.7 g/L, which is at a reduction rate of 13% compared with the initial urea content, while no urea reduction is found in broth of *B. amyloliquefaciens* JY06.

Example 4: Reduction of EC by *B. amyloliquefaciens* JP21

Step (1) is carried out according to EXAMPLE 3.

(2) Inoculation and grains fermentation: seed culture is obtained and inoculated into the medium containing 10 g/L urea and 5 g/L glucose, and then incubated at 37° C. for 24 h.

(3) Results: The EC concentration in the culture broth is detected. It is found that, EC in broth of *B. amyloliquefaciens* JP21 is 9.2 g/L, which is at a reduction rate of 8% compared with the initial EC content, while broth of *B. amyloliquefaciens* JY06 shows no EC reduction.

Example 5: Effect of Inoculation Size on Grains for Fermentation (1) Cells preparation: Colony of *B. amyloliquefaciens* JP21 is picked and inoculated into LB medium, after been incubated at 37° C. for 24 h, culture broth is centrifuged at 8000 rpm for 5 min; strains are collected and resuspended by sterile saline.

(2) Grains fermentation: The cells suspension at a final concentration of $1 \sim 9 \times 10^7$ CFU/g is inoculated to the grains with different volume of 5, 10, 20, and 30 mL, respectively. The resulting grains are incubated and fermented at 28~30° C. for 5 days.

(3) Results: Condition of fermented grains is observed. It shows that, each of the 100 g fermented grains that with 20 mL or 30 mL inoculation volume changed from solid to semi-solid after 5 days anaerobic fermentation, which is greatly distinguished from the real fermentation condition. Besides, the fermented grains with 20 mL or 30 mL inoculation volume shows the odor, acid characteristics of rancidity, indicating microbial system of the fermented grains has been changed. On the contract, each of the 100 g fermented grains with 5 mL or 10 mL inoculation volume keeps normal morphology and smell, which is consistent with normal fermented grains.

Example 6: Comparison of the Urea and EC Reduction Capability of *B. amyloliquefaciens* JY06 to that of *B. amyloliquefaciens* JP21

(1) Culture preparation: *B. amyloliquefaciens* JP21 and *B. amyloliquefaciens* JY06 are cultivated according to EXAMPLE 5.

(2) Inoculation: The bacterial culture is centrifuged at 8000 rpm for 5 min, strains are collected and resuspended in 0.85% NaCl. The cells suspension at a final concentration of $1 \sim 9 \times 10^6$ CFU/g is inoculated into the grains with volume of 5~10 mL.

(3) Grains fermentation: The grains prepared from step (2) is incubated and fermented at 28~30° C. for 5 days.

Control: Grains without strains inoculation that incubate and ferment under the same condition according to step (3) is set as the control. The initial concentration of EC and urea in grains is 15 µg/kg and 20 mg/kg, respectively.

(4) Results: Content of EC and urea in the fermented grains is determined (as shown in FIG. 1). The EC concentration of fermented grains for the control maintains at about 15 µg/kg, while EC in fermented grains that inoculated with $1 \sim 9 \times 10^6$ CFU/g *B. amyloliquefaciens* JP21 and JY06 are 11 µg/kg and 14 µg/kg, respectively, indicating the significant reduction of EC during the fermentation by the addition of $1 \sim 9 \times 10^6$ CFU/g *B. amyloliquefaciens* JP21, while *B. amyloliquefaciens* JY06 shows little effects on the reduction of EC.

The urea concentration of fermented grains (Control) decreases from 20 mg/kg to 19 mg/kg, while the final urea concentration in 5-days fermented grains that inoculated with $1 \sim 9 \times 10^6$ CFU/g *B. amyloliquefaciens* JP21 and JY06 are 17 mg/kg and 19 mg/kg, respectively, indicating a slight reduction of urea in grains by *B. amyloliquefaciens* JP21 and *B. amyloliquefaciens* JY06.

Example 7: Effect of Addition of *B. amyloliquefaciens* JY06 and *B. amyloliquefaciens* JP21 on Urea and EC Reduction (1) Culture preparation is carried out according to EXAMPLE 6.

(2) Inoculation: The bacterial culture is centrifuged at 8000 rpm for 5 min; strains are collected and resuspended in 0.85% NaCl. The cells suspension at a final concentration of $1\sim9\times10^7$ CFU/g is inoculated to the grains with volume of 5~10 mL, respectively.

(3) Grains fermentation: The grains prepared from step (2) is incubated and fermented at 28~30° C. for 5 days.

Figure 2:
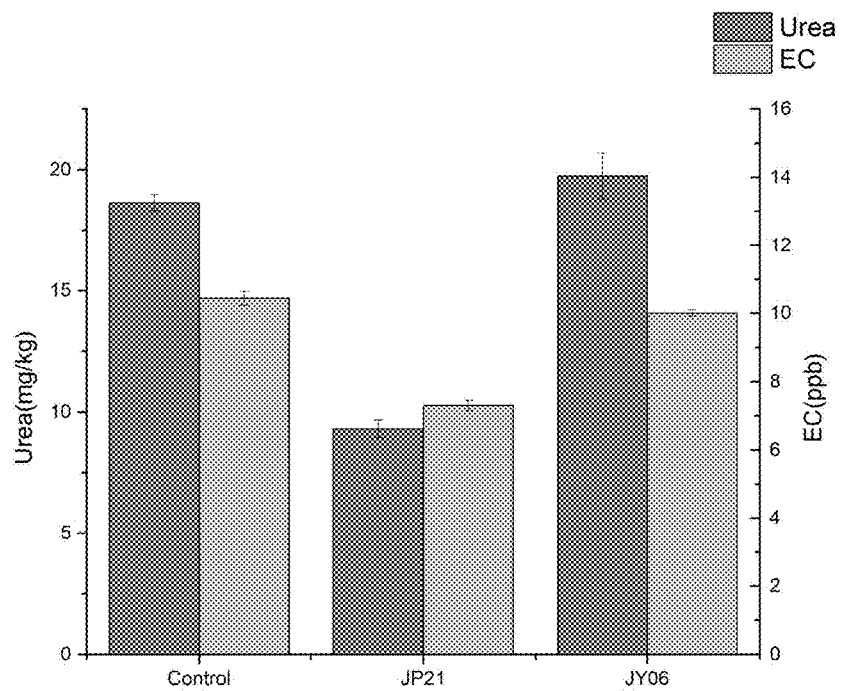
FIG. 2. EC and urea concentration of fermented grains that inoculated with B. amyloliquefaciens JP21 ($1\sim9\times10^7$ CFU/g) and B. amyloliquefaciens JY06 ($1\sim9\times10^7$ CFU/g) respectively.

(4) Results: EC and urea content in fermented grains are determined (as shown in FIG. 2).

The EC concentration of fermented grains (Control) maintains at about 15 μg/kg, while EC in fermented grains with $1\sim9\times10^6$ CFU/g inoculation of *B. amyloliquefaciens* JP21 or JY06 is 10 μg/kg and 14 μg/kg, respectively, indicating inoculation of $1\sim9\times10^7$ CFU/g *B. amyloliquefaciens* JP21 greatly helps to reduce EC content during the grains fermentation while *B. amyloliquefaciens* JY06 showed little effects.

The urea concentration of fermented grains (Control) decreases from 20 mg/kg to 19 mg/kg, while final urea concentration in 5 days fermented grains with $1\sim9\times10^6$ CFU/g inoculation of *B. amyloliquefaciens* JP21 and JY06 are 9 mg/kg and 20 mg/kg, respectively, indicating $1\sim9\times10^6$ CFU/g inoculation of *B. amyloliquefaciens* JP21 significantly reduces urea content during the fermentation while *B. amyloliquefaciens* JY06 showed little effects.

(5) Scale-up fermentation: The cells suspension is inoculated at final concentration of $1\sim9\times10^7$ CFU/g into volume of 1 L grains for fermentation (each 100 g grains are inoculated with 5~10 mL cells suspension), and fermented under the same condition with above method. The results show that, content of both EC and urea reduces, meanwhile the flavor of the fermented grains has no significant changes.

Example 8: Comparison of the Effect of Urea and EC Reduction by *B. amyloliquefaciens* JY06 and *B. amyloliquefaciens* JP21

(1) Culture preparation is carried according to EXAMPLE 7.

(2) Inoculation: The culture broth is centrifuged at 8000 rpm for 5 min; strains are collected and resuspended by sterile saline. The cells suspension at a final concentration of $1\sim9\times10^7$ CFU/g is inoculated to the grains with volume of 5~10 mL, respectively.

(3) Grains fermentation: The grains prepared from step (2) is incubated and fermented at 28~30° C. for 70 days.

(4) Results: EC and urea in fermented grains that fermented for 5 d, 20 d, and 70 d are determined. The initial content of EC and urea in grains are 32 μg/kg and 39 mg/kg respectively. Concentration of EC in grains on day 20 increased dramatically, which may result from the production of ethanol production during the fermentation. (Table 1)

(5) Reflux of fermented grains with ethanol: 20 g of fermented grains is mixed with deionized water and ethanol with a final concentration of 65%, the resulting mixture is transferred to a 250 mL flask and refluxed at 85° C. for 45 min to make sure the complete reaction of precursors with ethanol. The grains mixed with *B. amyloliquefaciens* JY06 or *B. amyloliquefaciens* JP21 are treated under the same condition. EC concentration of the resulting solution is determined through GC-MS. The EC concentration of the control is 89 μg/kg, grains that inoculated with *B. amyloliquefaciens* JY06 and *B. amyloliquefaciens* JP21 leads to 73 μg/L and 64 μg/L after the reflux reaction, which indicating the reduction of EC by *B. amyloliquefaciens* JY06 and *B. amyloliquefaciens* JP21 during the liquor production process.

TABLE 1

Concentration of EC and urea in fermented grains

| Stains for incubation | Fermentation Time (d) | EC | Urea |
|---|---|---|---|
| *B. amyloliquefaciens* JY06 | 0 | 32 | 39 |
| | 5 | 35 | 42 |
| | 20 | 50 | 42 |
| | 70 | 47 | 53 |
| *B. amyloliquefaciens* JP21 | 0 | 32 | 40 |
| | 5 | 33 | 36 |
| | 20 | 46 | 37 |
| | 70 | 43 | 48 |
| Control | 0 | 32 | 40 |
| | 5 | 38 | 41 |
| | 20 | 53 | 42 |
| | 70 | 52 | 53 |

Example 9: Effect of *B. amyloliquefaciens* JP21 and Urease on Urea and EC Reduction Since the rapid increase of EC during the initial 20 days fermentation, EC precursors in the fermented grains need to be reduced. The initial concentration of EC and urea of the grains in the present EXAMPLE 9 is 35 μg/kg and 35 mg/kg, respectively.

(1) Seed incubation: The *Lactobacillus reuteri* is inoculated into MRS medium, incubated at 30° C. for 72 h;

(2) Preparation of crude enzyme: the culture broth of step (1) is centrifuged; cells are collected and resuspended using 20 mM, pH 7.0 PBS solution; 0.1 mm-diameter glass beads is added for wall-breaking, after cells' wall breaking, the resulting solution is centrifuged at 10000 rpm for 10 minutes, the supernatant is collected and crude enzyme is obtained.

(3) Grains fermentation: The crude enzyme produced by *L. reuteri* and 15 mL cells suspension of *B. amyloliquefaciens* JP21 is inoculated into 150 g grains for fermentation, the final concentration of urease is 0.18 U/g grains, and the final concentration of *B. amyloliquefaciens* JP21 is $1-9\times10^7$ CFU/g. The grains after inoculation is fermented anaerobic at 28~30° C. for 70 days, which is named as Group C.

Meanwhile, the grains without *B. amyloliquefaciens* JP21 or urease inoculation is fermented under the same condition according to step (3), which is named as Group A.

Grains only inoculated with *B. amyloliquefaciens* JP21 is fermented under the same condition according to step (3), which is named as Group B.

The fermented grains from different groups that fermented for 0 d, 5 d, 10 d, 20 d, 30 d, 45 d, 60 d, and 70 d is collected at a quality of 10 g for EC and urea determination.

(4) Results: As shown in Table 2, the urea content of fermented grains from Group A increases to 45 mg/kg during 70 days fermentation. Compared with the Group A, Group B shows 11% urea reduction for 70 days fermentation. Besides, the urea content in fermented grains from Group C decreases more than 60% during the initial 20 days, followed by minor decrease in the next 50 days. The urea content reduces 43% by urease and *B. amyloliquefaciens* JP21 when the fermentation is done. which indicating combination of urease and *B. amyloliquefaciens* JP21 is effective in elimination of urea.

As shown in Table 2, EC concentration in fermented grains from Group A increases from 35 μg/kg to 58 μg/kg during the 70 days fermentation, while that decreases 16% in Group B and 32% in Group C. It can be concluded that, addition of urease and *B. amyloliquefaciens* JP21 can remarkably eliminate EC formation during grains fermentation.

Figure 3:
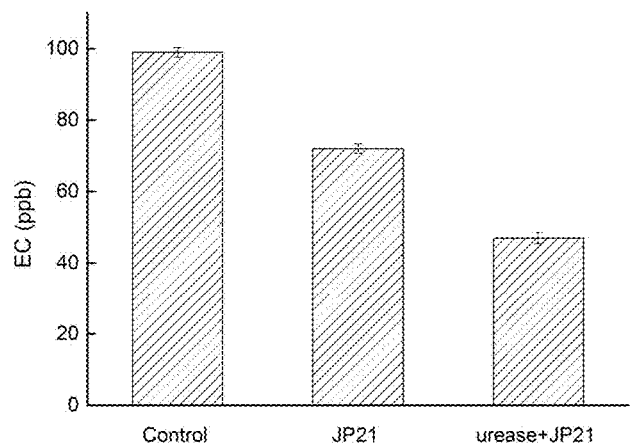
FIG. 3. Concentration of EC in distilled solution that prepared from fermented grains.

(5) Reflux of fermented grains with ethanol: The reflux reaction is carried out for fermented grains from different groups according to EXAMPLE 8. FIG. 3 shows that, EC content of the distilled solution from Group A is 99 µg/kg, which is 41 µg/kg higher than that from fermented grains (at end of the fermentation meanwhile the beginning of the distillation). Compared with the Group A, the content of EC in distilled solution decreases 25% in Group B and 52% in Group C, indicating *B. amyloliquefaciens* JP21 has capability of reducing EC concentration during the liquor production process including grains fermentation and distillation process. Moreover, inoculation of *B. amyloliquefaciens* JP21 and urease shows better effects.

TABLE 2

Concentration of EC and urea in fermented grains

| Group | Fermentation Time (d) | EC(µg/kg) | Urea(mg/kg) |
| --- | --- | --- | --- |
| Group A | 0 | 35 | 35 |
| | 5 | 37 | 39 |
| | 10 | 39 | 43 |
| | 20 | 53 | 46 |
| | 30 | 49 | 44 |
| | 45 | 55 | 40 |
| | 60 | 57 | 41 |
| | 70 | 58 | 41 |
| Group B | 0 | 35 | 35 |
| | 5 | 30 | 34 |
| | 10 | 34 | 36 |
| | 20 | 44 | 41 |
| | 30 | 43 | 35 |
| | 45 | 48 | 36 |
| | 60 | 46 | 37 |
| | 70 | 48 | 41 |
| Group C | 0 | 35 | 35 |
| | 5 | 26 | 12 |
| | 10 | 27 | 13 |
| | 20 | 30 | 18 |
| | 30 | 28 | 20 |
| | 45 | 30 | 20 |
| | 60 | 32 | 23 |
| | 70 | 36 | 26 |

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for reducing ethyl carbamate (EC) and its precursors levels, comprising inoculating $1$-$9 \times 10^7$ CFU/g *Bacillus amyloliquefaciens* (*B. amyloliquefaciens*) into grains for fermentation; wherein g is gram of weight of the grains for fermentation; wherein said *B. amyloliquefaciens* is *B. amyloliquefaciens* JP21, which is deposited in China Center for Type Culture Collection in Wuhan University, Wuhan. Hubei. China on Sep. 19, 2016 with Accession No. CCTCC No: M 2016499.

2. The method of claim 1, wherein said *B. amyloliquefaciens* is inoculated before grain fermentation begins.

3. The method of claim 1, comprising inoculating 5-10 mL of *B. amyloliquefaciens* cell suspension/100 g grains into the grain fermentation.

4. The method of claim 1, comprising obtaining the *B. amyloliquefaciens* from inoculating into a LB medium and incubating at 37° C. for 24-48 h.

5. The method of claim 1, wherein said *B. amyloliquefaciens* is inoculated into grains with urease before the grain fermentation begins.

6. The method of claim 5, wherein said urease is produced from *Lactobacillus reuteri*.

7. The method of claim 1, the method comprising the steps of: 1) *B. amyloliquefaciens* collection: inoculating the *B. amyloliquefaciens* into LB medium, and incubating at 37° C. for 24-48 h; centrifuging the resulting broth, collecting stain precipitation and then resuspending by physiological saline; 2) strain inoculation: inoculating *B. amyloliquefaciens* cells suspension at concentration of $1$-$9 \times 10^7$ CFU/g into grains for fermentation, wherein the volume of the *B. amyloliquefaciens* suspension is 5-10 mL/100 g grains; and 3) grains fermentation: incubating the grains under 28-30° C.

8. The method of claim 1, the method comprising the steps of: 1) strain inoculation: inoculating *B. amyloliquefaciens* cells suspension at concentration of $1$-$9 \times 10^7$ CFU/g into grains for fermentation, wherein the volume of the *B. amyloliquefaciens* suspension is 5-10 mL/100 g grains; and 2) grains fermentation: incubating the grains under 28-30° C.

* * * * *